United States Patent [19]

Ibsen et al.

[11] Patent Number: 5,009,709
[45] Date of Patent: Apr. 23, 1991

[54] STRONG DENTAL PORCELAIN AND METHOD FOR ITS MANUFACTURE

[75] Inventors: Robert L. Ibsen; Thomas C. Chadwick; Sally A. Pritchard, all of Santa Maria, Calif.

[73] Assignee: Den-Mat Corporation, Santa Maria, Calif.

[21] Appl. No.: 548,294

[22] Filed: Jul. 3, 1990

Related U.S. Application Data

[63] Continuation of Ser. No. 244,853, Sep. 15, 1988, abandoned.

[51] Int. Cl.$^5$ .................. A61C 13/00; A61C 13/083; C01K 3/00
[52] U.S. Cl. .................. 106/35; 106/38.3; 433/199.1; 433/201.1; 433/202.1; 433/212.1; 501/15; 501/17; 501/70
[58] Field of Search .................. 106/35, 38.3; 433/199.1, 213, 202.1, 228.1, 201.1, 218, 212.1, 206, 207; 501/15, 16, 17, 66, 69, 70

[56] References Cited

U.S. PATENT DOCUMENTS

| | | | |
|---|---|---|---|
| 3,052,982 | 9/1962 | Weinstein et al. | 106/35 |
| 3,973,972 | 8/1976 | Muller | 106/35 |
| 4,515,634 | 5/1985 | Wu et al. | 433/202.1 |
| 4,746,578 | 5/1988 | Kondo et al. | 501/15 |
| 4,798,536 | 1/1989 | Katz | 433/199.1 |
| 4,812,423 | 3/1989 | Kodama et al. | 501/66 |
| 4,851,372 | 7/1989 | Lindig et al. | 501/70 |
| 4,879,136 | 11/1989 | Polz | 106/35 |

Primary Examiner—Paul Lieberman
Assistant Examiner—John Boyd
Attorney, Agent, or Firm—Owen, Wickersham & Erickson

[57] ABSTRACT

A dental porcelain having the following composition:

| Ingredient | Weight by Percent |
|---|---|
| $SiO_2$ | 52.7%–64.6% |
| $Al_2O_3$ | 6.3%–16.4% |
| $Li_2O$ | 0%–0.5% |
| $Na_2O$ | 3.9%–14.2% |
| $K_2O$ | 4.5%–11.7% |
| MgO | 0%–.3% |
| CaO | 1.6%–3.3% |
| SrO | 0.9%–2.3% |
| BaO | 0.3%–8.1% |
| $TiO_2$ | 0.1%–3.6% |
| $B_2O_3$ | 0.2%–5.0% | made by blending powdered first-fire frit with pacifiers, heating this first-fire frit to 2000° F., and rapidly cooling the charge.

13 Claims, 4 Drawing Sheets

FIRST FIRE FRIT FIRED AT 1820° F

FIRST FIRE FRIT FIRED AT 1820 °F

FIRST FIRE FRIT FIRED AT 1925 °F

SECOND FIRE FRIT FIRED AT 1820 °F

SECOND FIRE FRIT FIRED AT 1925 °F

STRONG DENTAL PORCELAIN AND METHOD FOR ITS MANUFACTURE

This is a continuation of co-pending application Ser. No. 07/244,853, filed on Sept. 15, 1988, now abandoned.

This invention relates to compositions for making improved fired dental porcelains, to improved fired porcelain, and to processes for making the improved porcelains. The invention provides production methods for producing strong porcelain which is especially well suited to the fabrication of porcelain veneers, which can be bonded to the surfaces of anterior and posterior teeth.

BACKGROUND OF THE INVENTION

The use of porcelain facings or veneers (also called porcelain laminates) to cover unsightly teeth and thereby improve their appearance was pioneered by Dr. Charles Pincus in 1928. Dr. Pincus fabricated his porcelain veneers by firing packed dental porcelain powder on platinum foil. All of this early work with porcelain laminates was done using dental porcelain that was fired at 1404° C. (2560° F.).

Because of the limited range of adhesives available at the time, veneers were cemented in place only temporarily. Because of their expense and the limitations imposed by the available adhesives, porcelain veneers were used primarily by movie stars during performances before the camera (for a detailed account of the early history of porcelain veneers see: *J. Cosmetic Dentistry*, 1 (3), 6–8 (1985).

During the 1970's great improvements were made in the area of dental adhesives, and the use of porcelain veneers became popular among the general public. Because of the limitations in the strengths of existing porcelain, the technique of building a metal substructure and firing porcelain to the outside was also developed. Although this technique was successful and useful, it had its limitations. Paramount among the difficulties associated with porcelain-metal restorations was the need to match the coefficient of thermal expansion of the porcelain and the underlying metal and the need to opacify heavily the porcelain, so that the metal substructure would remain well hidden. The use of porcelain-fused-to-metal construction also made it possible to fabricate more complicated structures, such as porcelain jacket crowns and bridges, but the previously mentioned problems and the difficulty of bonding metal reliably to tooth structure made all-porcelain restorations a desirable goal. (For an extensive review of the application of porcelain to metal see John W. McLean, "The Science and Art of Dental Ceramics—Volume 1: The Nature of Dental Ceramics and Their Clinical Use", Quintessence Publishing Co., Inc., Chicago, 1979).

In order to avoid the need for a metal substructure, much effort has been directed to strengthening dental porcelain. Attempts to strengthen dental porcelain have usually involved the inclusion of strengthening oxide particles in the base porcelain. Examples of strengthening oxides include zirconium oxide (See R. Morena, P. E. Lockwood, A. L. Evans, and C. W. Fairhurst, "Toughening of Dental Porcelain by Tetragonal $ZrO_2$ Additions", *J. Am. Ceram. Soc.* 69 (4), C-75–C-77 (1986)) and aluminum oxide (see M. H. Brown and S. E. Sorenson, *J. Prosthet. Dent.* 42 (5), 507–574 (1979)). The inclusion of strengthening oxides opacifies the porcelain and makes simultaneous control of opacity and strength impossible. The tensile strengths of both traditional dental porcelain as well as metal oxide strengthened porcelain as measured for the present work and taken from various sources in the literature are presented in Table 1.

TABLE 1

Tensile Strengths of Prior-Art Porcelains

| Porcelain | Tensile Strength (lbs/in$^2$) |
|---|---|
| Vitadur N Aluminous Body | 5887 ± 1294 |
| Vitadur N Aluminous Incisal | 5972 ± 1294 |
| Trubyte Aluminous Incisal | 3626 ± 668 |
| Steele's Aluminous Incisal | 5972 ± 796 |
| Trubyte Aluminous Body | 4223 ± 355 |
| Steele's Aluminous Incisal | 5986 ± 882 |
| Vitadur N-Dentine | 8200 ± 1700 |
| Pentron-Shade A1 | 8300 ± 900 |
| Feldspar Dental Porcelain | about 5000 |

An ideal porcelain for the fabrication of all-porcelain veneers, crowns and bridges should possess high strength. Ideally, it should possess the strength of the metal-oxide-reinforced porcelains. It should be available in a range of opacities which ideally could run from very opaque to clear. The coefficient of thermal expansion of the porcelain should match the coefficients of thermal expansion of the bonding agents and underlying teeth. It should be available in a variety of shades, and the colorants should be incorporated in, rather than painted on, the porcelain.

Finally, the porcelain should be easy to fabricate by either the platinum foil or refractory model fabrication techniques. It should not show a pronounced tendency to separate during the initial firing, and any separation cracks that do form should heal easily rather than separate further. The maturing temperature should be below 1093° C. (2000° F.) to avoid any unnecessarily severe service for the vacuum furnaces. As a final point, the coefficient of thermal expansion should be less than $15 \times 10^{-6}$ °C.$^{-1}$ in order to avoid difficulty in matching refractory expansion to that of the porcelain.

DETAILED DESCRIPTION OF THE INVENTION

The invention relates to a high strength, esthetically pleasing dental porcelain composition and its method of manufacture. The dental porcelain of this invention may be fabricated either by application of the porcelain to platinum foil or a refractory model whose coefficient of thermal expansion is adjusted to match that of the porcelain. The dental porcelain of this invention exhibits tensile strengths in excess of aluminum-oxide-reinforced dental porcelains. This great strength is achieved without the addition of strengthening oxides, thereby avoiding the problem of opacification and reduced esthetics which attend the use of strengthening oxides It is possible with this porcelain to fabricate a veneer that is thinner and more translucent than those used with existing porcelains.

The coefficient of thermal expansion of the dental porcelain composition which is the subject of this invention is almost exactly matched to the thermal expansion of the tooth structure and to the composite adhesives which are used to bond porcelain restorations to tooth structure. The high strength and the matched coefficient of thermal expansion enable the dentist to place restorations made of this porcelain without fear of breakage during handling or debonding after placement due to thermal expansion incompatibility. The extra strength of this porcelain enable the dental technician to fabricate thin laminates which can then be removed from a platinum or refractory substrate without fear of fracture.

The porcelain dental restorative of this invention employs a blend of colored and uncolored frits, formulated to achieve the desired shade or shades, and ground, screened, and blended to provide a material which will pack to high density on a refractory or platinum foil. The colored and uncolored frits are themselves the products of a two-firing or two frit process which comprises blending spinel pigments, titanium dioxide or other suitable opacifier, and a previously prepared base frit, and then firing the resulting blend under conditions where the rate of dissolution of the opacifier is low and the rate of sintering of the ceramic particles is high enough to form a thoroughly fused product.

The composition of the base frit should fall within the following ranges, the percentages referring to the elemental composition of the frit with the elements expressed as their oxides:

TABLE 2

| Base Frit Composition | |
| --- | --- |
| Ingredient | Weight by Percent |
| $SiO_2$ | 56%–66% |
| $Al_2O_3$ | 13%–18% |
| $Li_2O$ | 0%–1% |
| $Na_2O$ | 0%–6% |
| $K_2O$ | 19%–31% |
| MgO | 0%–1% |
| CaO | 0%–2.5% |
| SrO | 0%–2% |
| BaO | 0%–3% |
| $TiO_2$ | 0%–2% |
| $B_2O_3$ | 0%–2% |

The base frit of this invention can be prepared by melting together suitable amounts of precursors, the quantities of which are chosen to produce the composition ranges discussed above. One suitable base frit can be made simply using a feldspar whose composition is

TABLE 3

| A Feldspar-Two-Glass and $Li_2CO_3$ Base Frit | |
| --- | --- |
| (1) Feldspar Composition | |
| Ingredient | Weight by Percent |
| $SiO_2$ | 64%–68% |
| $Al_2O_3$ | 17%–19% |
| $Na_2O$ | 2%–4% |
| $K_2O$ | 9%–11% |
| CaO, | 0.1%–1.0% |
| (2) as a second component, a first glass, whose composition is approximately | |
| Ingredient | Weight by Percent |
| $SiO_2$ | 54%–58% |
| $Al_2O_3$ | 5%–9% |
| $Na_2O$ | 4%–8% |
| $K_2O$ | 18%–22% |
| MgO | 0%–4% |
| CaO, and | 0%–8% |
| (3) as a third component a second glass, whose composition is approximately | |
| Ingredient | Weight by Percent |
| $SiO_2$ | 42%–48% |
| $Al_2O_3$ | 0%–2% |
| $Na_2O$ | 18%–22% |
| CaO | 0%–4% |
| SrO | 0%–4% |
| BaO | 10%–14% |
| $TiO_2$ | 4%–8% |

TABLE 3-continued

| A Feldspar-Two-Glass and $Li_2CO_3$ Base Frit | |
| --- | --- |
| $B_2O_3$ | 6%–10%, |
| and | |
| (4) lithium carbonate is present (0%–3%) as a fourth component. | |

Other components besides the preferred components listed above are also suitable as raw materials. These include silica (either quartz, cristobalite, or amorphous silica), sodium carbonate, potassium carbonate, magnesium carbonate (both normal as well as basic carbonates), calcium carbonate, dolomite, and barium carbonate, as well as the oxides which correspond to these carbonates. These alternative formulations may be devised by the usual batch sheet calculations, which are well known to those who are skilled in the art.

The preparation of the base frit is accomplished by the usual techniques of ceramic fabrication. The materials are preferably first ground, then screened to pass a 200 mesh U.S. series screen. Next, the powders are blended, either in a conical blender or other suitable blending device, to produce a uniform, homogenous powder. The powdered blend is then packed into suitable refractory containers and fired to at least 2250° F. and preferably to 2350° F. to provide a uniform homogenous melt. The charge is then cooled slowly, and the frit blocks are removed from the kiln and crushed. The resulting chips are then ground to yield a powder which passes a 200 mesh U.S. series screen.

Even through the porcelain is not intended for application to metal, some degree of opacification is frequently necessary, since the frit that results from the first firing is quite clear. Since opacifiers at low levels of addition tend to dissolve in the melt if added for the first fritting, they are incorporated in a mixture of base frit and pigments to produce colored, opacified second-fire frits which can later be blended to produce colored dental porcelain.

Titanium dioxide is the preferred opacifier, but other opacifiers, such as $SnO_2$, $Al_2O_3$, ZnO, and $CeO_2$, have proven useful Zirconium silicate can also be used.

The raw materials for the second fritting should be ground to pass a 200 mesh U.S. series screen, and the materials blended until homogeneous in a conical blender or other similar device. The blended powder is then packed into suitable refractory containers and fired to at least 1950° F. and preferably to 2000° F. for a time sufficient to fuse the ceramic powders thoroughly.

After the blended powder has been fired, to complete the second firing of the frit, it is crushed and then ball milled, to provide a product with the proper particle-size distribution. In a preferred embodiment of the invention, no more than 50% of the ground material should pass a 325 U.S. series screen. Both the plain opacified frit (frit which has only opacifier added prior to the second fritting operation) as well as colored opacified frit should be milled to the same particle-size distribution.

The finished ceramic dental restorative is formulated by blending colored, opacified frit, as well as uncolored opacified frit. If greater clarity in the finished porcelain is desired, colored or uncolored unopacified second-fire frit can be produced. The techniques for matching colors are well known to those skilled in the art. It should be recognized that the color blending scheme can be altered to include more than one color in a frit used for blending, and such a modification lies within the scope of the invention.

Although the original intention for incorporating the second firing was to provide a uniformly opacified, colored frit, several unanticipated benefits were also obtained. The tensile strength of the twice-fired frit material is substantially increased over the single-fired frit material. For example, where first-fire frit typically has tensile strengths of $9600\pm1200$ lb/in$^2$, the second-fire strength is increased 45% into $14,000\pm1400$ lb/in$^2$.

The porcelain of the invention exhibits a much reduced tendency to crawl, relative to porcelain produced from first-fire frit, when it is built and fired to produce laminates. The tendency to crawl was studied by first preparing twenty-one blends of $-100/+200$, $-200/+325$, and $-325$ mesh (U.S. Series) of both first-fire and second-fire frit. These blends were then used to build two test porcelain veneers of each test mixture, and these veneers were then fired, some at 1820° F. and some at 1925° F. The tendency to mud-crack was evaluated by counting the total number of separation cracks in the two veneers. These numbers were then plotted on a triaxial blending diagram

THE CRAWLING EXPERIMENTS

Figure 1:
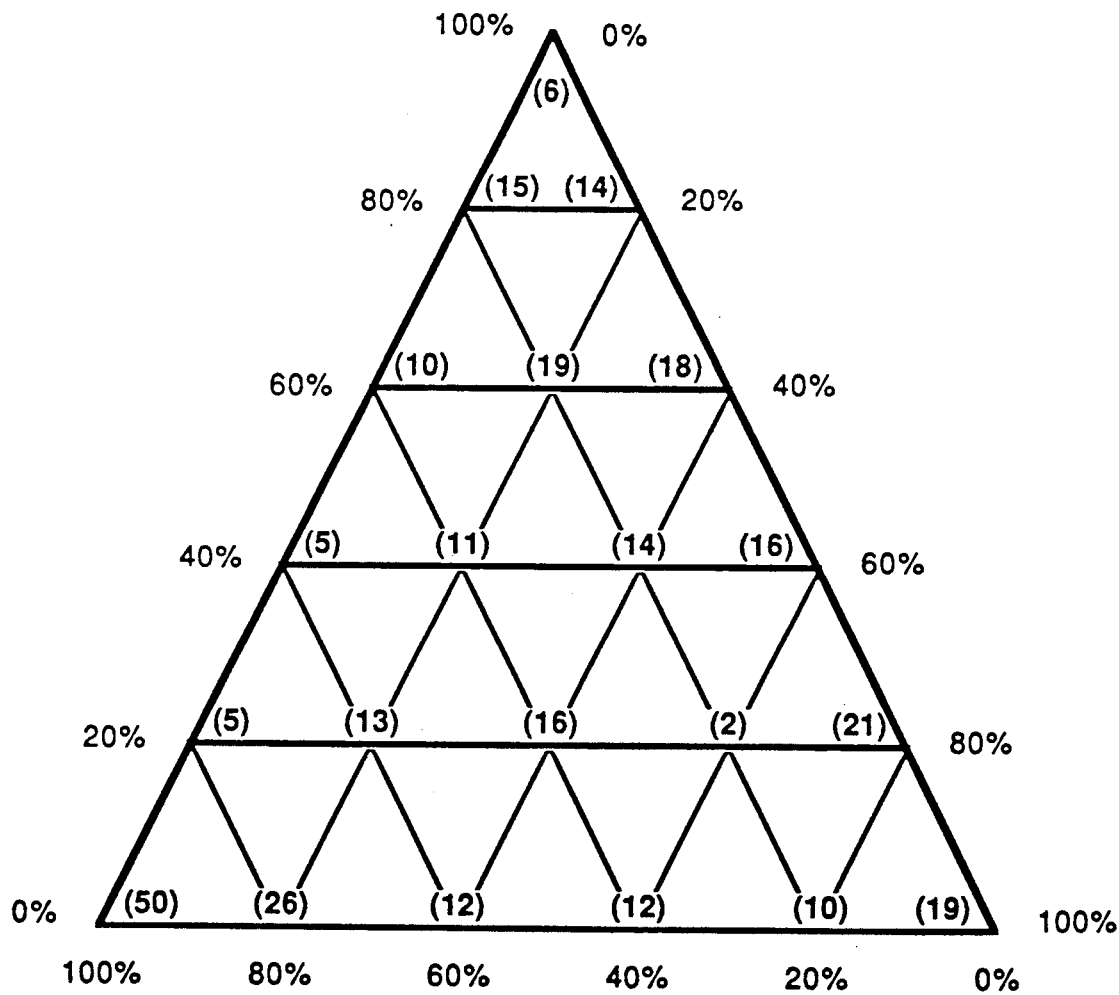
FIG. 1 is a triaxial diagram of the results of a crawling experiment, obtained from first-fire frit fired at 1820° F. The figures in parentheses in each of FIGS. 1-4 denotes the total number of cracks found in two test laminates of each experiment after firing.
Figure 2:
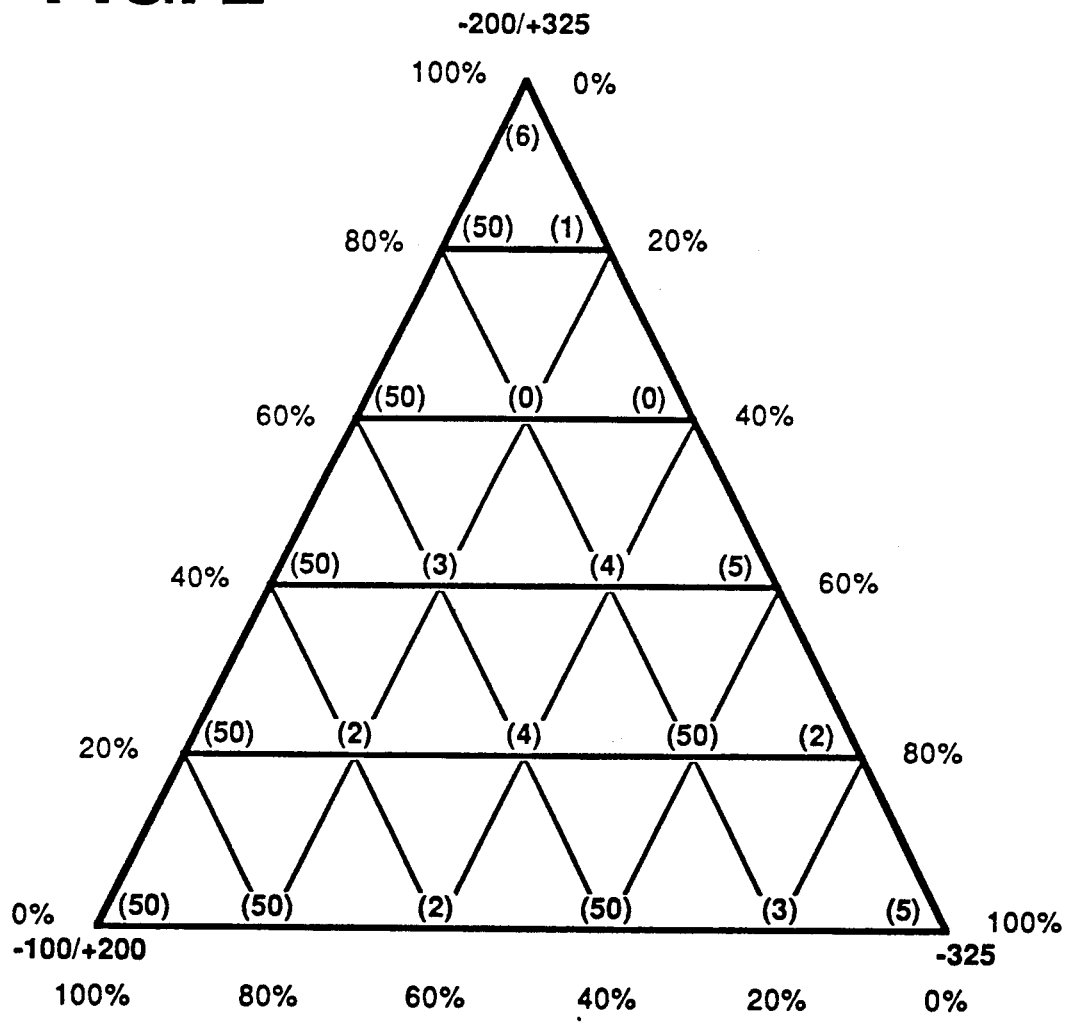
FIG. 2 is a similar diagram for first-fire frit fired at 1925° F.

With reference to FIG. 1, it can be seen that all first-fire frit blends showed a marked tendency to crack when fired at 1820° F. When the firing temperature was raised to 1925° F. (FIG. 2) the frit performed somewhat better, with mixtures in the center of the blending diagram and along the edge corresponding to binary blends of $-200/+325$ and $-325$ particle sizes. Everywhere else, separation was severe.

Figure 3:
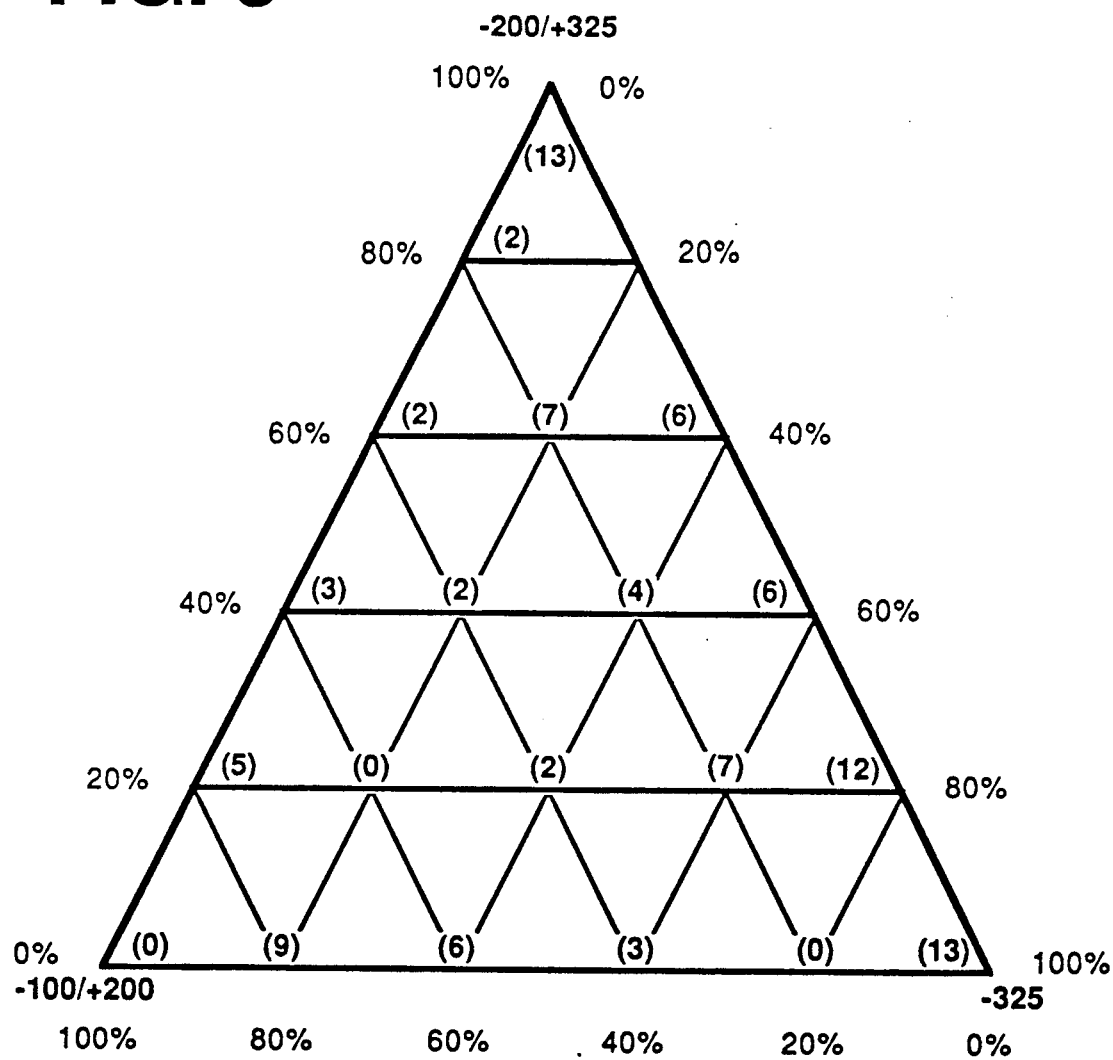
FIG. 3 is a similar diagram of the results obtained from second-fire frit fired at 1820° F.
Figure 4:
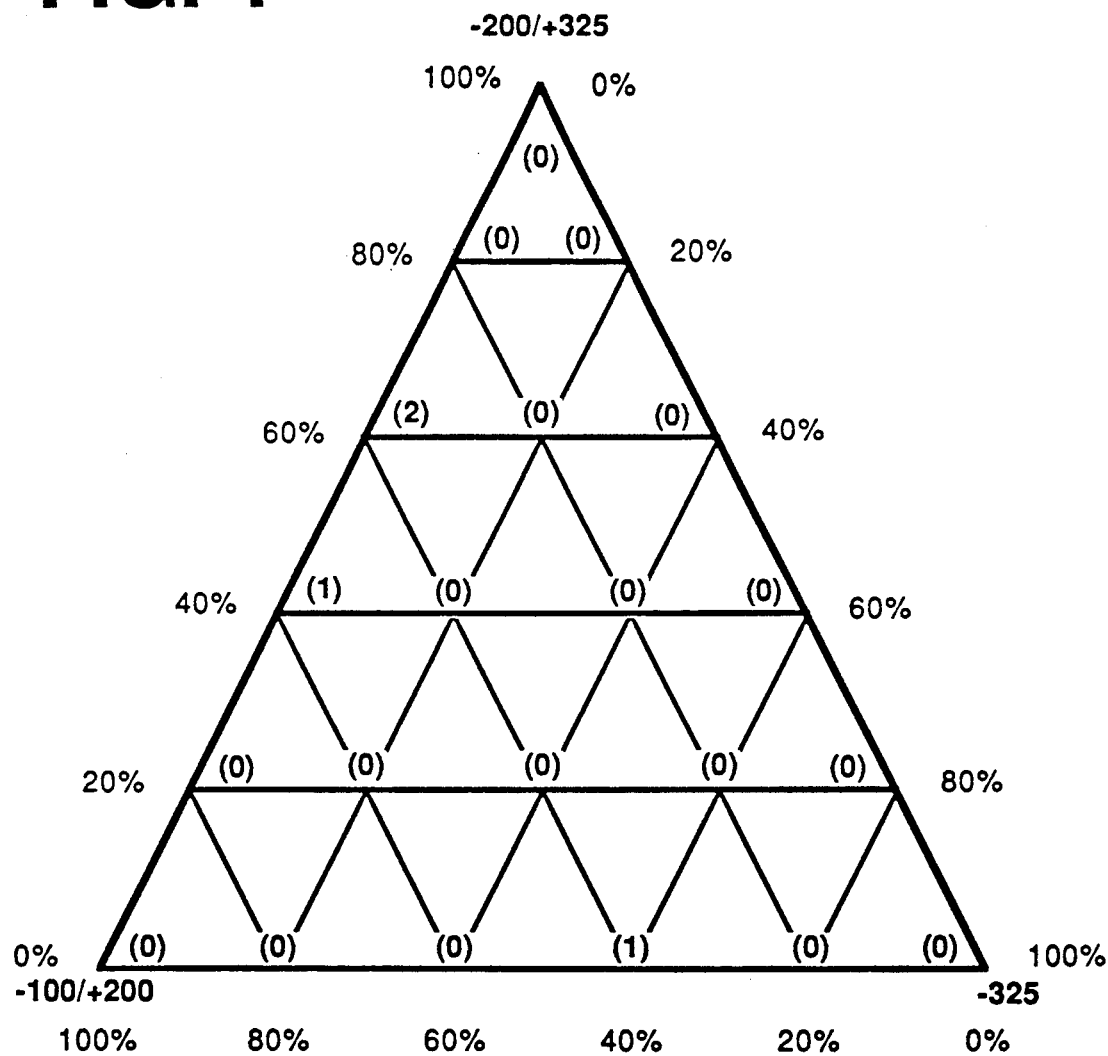
FIG. 4 is a similar diagram of the results obtained from second-fire frit fired at 1925° F.

Second-fire frit performed much differently. When fired at 1820° F. (FIG. 3), only moderate amounts of separation were noted. When the second-fire frit test samples were fired at 1925° F. (FIG. 4) separation cracks almost completely disappeared. As predicted by theory, separation was most severe for samples which contained narrow ranges of particle sizes.

EXAMPLE 1

Production of a Base Frit

A 4165 g portion of feldspar comprising

| Ingredient | Weight by Percent |
|---|---|
| SiO$_2$ | 67.1% |
| Al$_2$O$_3$ | 18.5% |
| Na$_2$O | 3.0% |
| K$_2$O | 10.5%, and |
| CaO | 0.9% | was mixed with 735 g of Glass 1,

| Ingredient | Weight by Percent |
|---|---|
| SiO$_2$ | 55.4% |
| Al$_2$O$_3$ | 7.19% |
| Na$_2$O | 6.68% |
| K$_2$O | 20.2% |
| MgO | 1.92% |
| CaO | 8.32% |
| SrO | 0.05% |
| BaO | 0.22% |
| TiO$_2$ | 0.02% |

100 g of Glass 2,

| Ingredient | Weight by Percent |
|---|---|
| SiO$_2$ | 46.0% |
| Al$_2$O$_3$ | 0.74% |
| Na$_2$O | 20.0% |
| K$_2$O | 0.06% |
| CaO | 3.8% |
| SrO | 3.5% |
| BaO | 12.5% |
| TiO$_2$ | 5.6%, and |
| B$_2$O$_3$ | 7.8% | and 62.5 g of lithium carbonate.

All components were ground to pass 200 mesh prior to blending. The powders were blended and ground together in a ball mill for two hours, and the blended powders were then packed into a fireclay crucible. The crucible and its contents were brought to 2350° F. in six hours and held at that temperature for an additional three hours. After the contents of the kiln had cooled to room temperature, the frit block was removed from the crucible, cleaned, and then crushed. The crushed frit was then ground to pass a $-325$ mesh screen. The powdered frit was pressed into discs (unfired diameter and thickness were 1.1 mm and 29.0 mm respectively) and fired at 1925° F. in order to evaluate the visual appearance. The tensile strength was determined by pressing the porcelain powder into pellets at a pressure of 6300 lb/in$^2$ (unfired pellet size was 4.0 mm $\times$ 12.2 mm diameter) and firing the pellets at 1925° F. on a cordierite support tray. The pellets were then placed on edge and crushed in an Instron Model 1000 testing machine. The tensile strength was calculated from the relationship:

Tensile strength = 2P/DT where

P = load (lbs) at failure
D = Diameter (inches)
T = Thickness (inches).

The frit produced in this example exhibited a tensile strength of $9588\pm1178$ lb/in$^2$.

EXAMPLE 2

Alternate Formulation of the Base Frit

A 3402 g portion of the feldspar of Example 1 was mixed with 1134 g of Glass 2 of Example 1, fired, worked up and tested for tensile strength as described in Example 1. The tensile strength of this frit as measured on test pellets matured at 1900° F. was $10341\pm672$ lb/in$^2$.

EXAMPLE 3

Alternate Formulation of the Base Frit

A 400 g portion of feldspar of Example 1 was mixed with 100 g of Glass 1 and 900 g of Glass 2, fired, worked up and tested for tensile strength as described in Example 1. The tensile strength of this frit, as measured on test pellets matured at 1825° F., was 11663±2013 lb/in².

EXAMPLE 4

Alternate Formulation of the Base Frit

A 17.214 kg portion of feldspar with the composition shown in Example 1 was mixed with 0.396 kg of the second glass of Example 1 and 0.246 kg of lithium carbonate. Additional components in the amounts shown in the following table were then added to the mixture to produce the alternate formulation.

| Component | Weight (Kg) |
| --- | --- |
| Glass: | |
| Ingredient | Weight by Percent |
| $SiO_2$ | 66.7% |
| $Al_2O_3$ | 2.4% |
| CaO | 4.2% |
| BaO | 2.8% |
| $Na_2O$ | 22.2% |
| $K_2O$ | 0.5% |
| MgO | 1.2% |
| | 1.271 |
| $K_2CO_3$ (potash) | 0.734 |
| $CaMg(CO_3)_2$ (dolomite) | 0.460 |
| $CaCO_3$ (whiting) | 0.142 |
| Silica | 0.055 |

All components were ground to −200 mesh (U.S. Series screen) prior to blending. After the batch had been blended and ground for two hours in a ball mill, it was screened to remove the aluminum oxide grinding balls, and the blended mixture was packed into cordierite saggers. The mixture was brought to 2350° F. in six hours and held at that temperature for three hours. After cooling to room temperature, the blocks of frit were cleaned, crushed, and ground, all as described previously. The frit produced by this method was indistinguishable petrographically and visually from frit produced by the methods of Example 1. The maturing temperature was 1935° F. and the tensile strength was 11400±1900 lb/in².

Based on the Examples 1–4, the ranges for the percentages of each of the ingredients comprising the porcelain mixture according to the present invention are as follows, as calculated in accordance with formula:

$$\frac{(W_F \times \%_{IF}) + (W_{G1} \times \%_{IG1}) + (W_{G2} \times \%_{IG2})}{\text{TOTAL WEIGHT}(W_F + W_{G1} + W_{G2} + W_{Li2O})}$$

where:
$W_F$ = Weight of Feldspar
$W_{G1}$ = Weight of Glass 1
$W_{G2}$ = Weight of Glass 2
$W_{Li2O}$ = Weight of Lithium Carbonate
$\%_{IF}$ = Percent of Ingredient in Feldspar
$\%_{IG1}$ = Percent of INgredient in Glass 1
$\%_{IG2}$ = Percent of Ingredient in Glass 2

These ranges of ingredients for the Examples 1–4 are as follows:

| | Examples 1,4 | Example 2 | Example 3 |
| --- | --- | --- | --- |
| $SiO_2$ | 64.6 | 61.8 | 52.7 |
| $Al_2O_3$ | 16.4 | 14.1 | 6.3 |
| $Li_2O$ | 0.5 | — | — |
| $Na_2O$ | 3.9 | 7.3 | 14.2 |
| $K_2O$ | 11.7 | 7.9 | 4.5 |
| MgO | 0.3 | — | 0.1 |
| CaO | 2.0 | 1.6 | 3.3 |
| SrO | 0.1 | 0.9 | 2.3 |
| BaO | 0.3 | 3.1 | 8.1 |
| $TiO_2$ | 0.1 | 1.4 | 3.6 |
| $B_2O_3$ | 0.2 | 2.0 | 5.0 |

EXAMPLE 5

Production of Opacified Frit

An 18.00 kg portion of base frit, produced and finely ground, using methods described in Example 1, was mixed with −325 mesh titanium dioxide, 135 g. The two components were blended in a ball mill for two hours. The balls were removed by screening, and the mixture was packed in cordierite saggers for firing. The temperature of the kiln was brought from room temperatures to 2000° F. in four hours. The material was held at 2000° F. for 0.75 hours and then immediately removed from the kiln. After the frit was cool, it was crushed and ground, using methods described in Example 1, and its appearance and tensile strength were evaluated using the methods described above. The tensile strength of the frit prepared by this method was 12800±2800 lb/in².

EXAMPLE 6

Preparation of Opacified, Colored, Second-Fire Frit

Colored frits were prepared following the method of Example 4, except that finely ground spinel pigments, in the amount of 360 g for the batch size described in Example 4, were incorporated in the blending step. The blended mixtures were then fired as described in Example 4. In this fashion yellow, pink, red-brown, grey, orange, and yellow/gray frits were prepared.

EXAMPLE 7

Formulation of Shade A1 by Blending Colored and Uncolored Opacified Ground Frits As an example of the production of the finished porcelain by blending basic colored frits, the preparation of Vita Shade A1 will be described. A 2100 g portion of opacified second-fire frit along with 290 g of yellow opacified frit, 1955 g of pink frit, 60 g of red-brown frit and 50 g of grey frit, all ground according to Example 6, were placed in a baffled five-gallon glass jar and mixed for one hour. The mixture was sampled to prepare a shade chip as described in Example 1, and the resulting chip was matched against an A1 Vita shade guide to confirm that the shades did match. If the shade does not match the desired shade, then appropriate colored frits can be added in small amounts to the mixing jar until an exact match is achieved.

In similar fashion, both Vita and Bioform shades can be prepared.

Thus, the invention includes the method of making dental porcelain by blending colored, opacified, powdered frits which have been prepared from the base frit. The method include grinding the base frit, opacifiers, and pigments while blending the ground components thoroughly. After packing the ground and blended powdered components in suitable refractory containers, the refractory containers and their contents are heated in a kiln to 2350° F. in six hours. They are then held at that temperature for approximately an additional three hours. This is followed by cooling the containers and their contents to room temperature. The resulting frit blocks are then removed and cleaned, followed by crushing and grinding the particles to pass a 200 mesh screen.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A base frit for dental porcelain, including in combination a portion of feldspar comprising:

| Ingredient | Weight by Percent |
| --- | --- |
| $SiO_2$ | 67.1% |
| $Al_2O_3$ | 18.5% |
| $Na_2O$ | 3.0% |
| $K_2O$ | 10.5%, and |
| CaO | 0.9% | mixed with a Glass 1, comprising:

| Ingredient | Weight by Percent |
| --- | --- |
| $SiO_2$ | 55.4% |
| $Al_2O_3$ | 7.19% |
| $Na_2O$ | 6.68% |
| $K_2O$ | 20.2% |
| MgO | 1.92% |
| CaO | 8.32% |
| SrO | 0.05% |
| BaO | 0.22% |
| $TiO_2$ | 0.02% | and then mixed with a Glass 2, comprising:

| Ingredient | Weight by Percent |
| --- | --- |
| $SiO_2$ | 46.0% |
| $Al_2O_3$ | 0.74% |
| $Na_2O$ | 20.0% |
| $K_2O$ | 0.06% |
| CaO | 3.8% |
| SrO | 3.5% |
| BaO | 12.5% |
| $TiO_2$ | 5.6% |
| $B_2O_3$ | 7.8%, | and then mixed with lithium carbonate.

2. A dental porcelain wherein in the base frit of claim 1:
all components have been ground to pass 200 mesh prior to blending and wherein during the blending they are all ground together,
the resultant mixture being fired at 2350° F.,
said fired product, after cooling to room temperature being crushed and ground to pass a −325 mesh screen and fired again at 1925° F.

3. The composition 1 wherein 82.9 parts by weight of feldspar, 14.6 parts by weight of glass 1 and 2.0 parts by weight of glass 2 are mixed with 1.5 parts by weight of lithium carbonate to produce 100 parts of base frit.

4. The composition of claim 1 wherein 75 parts by weight of feldspar and 25 parts by weight of glass 2 are mixed to produce 100 parts of base frit.

5. The composition of claim 1 wherein 28.6 parts of feldspar, 7.1 parts of glass 1 and 64.3 parts of glass 2 are mixed to produce 100 parts of base frit.

6. A method for making base frit for dental porcelain, comprising mixing a feldspar compound of

| Ingredient | Weight by Percent |
| --- | --- |
| $SiO_2$ | 67.1% |
| $Al_2O_3$ | 18.5% |
| $Na_2O$ | 3.0% |
| $K_2O$ | 10.5%, and |
| CaO | 0.9% | with a Glass 1, comprising:

| Ingredient | Weight by Percent |
| --- | --- |
| $SiO_2$ | 55.4% |
| $Al_2O_3$ | 7.19% |
| $Na_2O$ | 6.68% |
| $K_2O$ | 20.2% |
| MgO | 1.92% |
| CaO | 8.32% |
| SrO | 0.05% |
| BaO | 0.22% |
| $TiO_2$ | 0.02% | and then mixing with a Glass 2, comprising:

| Ingredient | Weight by Percent |
| --- | --- |
| $SiO_2$ | 46.0% |
| $Al_2O_3$ | 0.74% |
| $Na_2O$ | 20.0% |
| $K_2O$ | 0.06% |
| CaO | 3.8% |
| SrO | 3.5% |
| BaO | 12.5% |
| $TiO_2$ | 5.6% |
| $B_2O_3$ | 7.8%, | and then mixing with lithium carbonate.

7. A method of making a dental porcelain by blending colored, opacified, powdered frits which have been prepared from the base frit of claim 6 by:
grinding said base frit, with opacifiers and pigments, while blending the ground components thoroughly,
packing the ground and blended powdered components in a suitable refractory container,
heating the refractory container and its contents in a kiln to 2350° F. in six hours and holding it at that temperature for an additional period of about three hours, cooling the container and its contents to room temperature,
removing the resulting frit block, and
cleaning, crushing, and grinding it to pass as 200 mesh screen.

8. The method of claim 7 wherein the cleaning, crushing, and grinding steps are followed by re-firing the resulting mixture.

9. The method of claim 7 wherein base frit ingredients are in proportion, by weight, of 4165:735:100:62.5.

10. The method of claim 7 wherein in the base frit the proportion by weight of the feldspar to glass 2 is 3402:1134.

11. The method of claim 7 wherein in the base frit the proportion by weight of feldspar:glass 1:glass 2 is 400:100:900.

12. The composition of claim 7 wherein in the base frit the proportion by weight of feldspar:glass 1: glass 2 is 17,214 to 396:246.

13. A dental porcelain having the following composition:

| Ingredient | Weight by Percent |
|---|---|
| $SiO_2$ | 52.7%–64.6% |
| $Al_2O_3$ | 6.3%–16.4% |
| $Li_2O$ | 0%–0.5% |
| $Na_2O$ | 3.9%–14.2% |
| $K_2O$ | 4.5%–11.7% |
| $MgO$ | 0%–.3% |
| $CaO$ | 1.6%–3.3% |
| $SrO$ | 0.9%–2.3% |
| $BaO$ | 0.3%–8.1% |
| $TiO_2$ | 0.1%–3.6% |
| $B_2O_3$ | 0.2%–5.0% |

* * * * *